United States Patent [19]

Sibrava et al.

[11] 4,276,982

[45] Jul. 7, 1981

[54] PRESSURE SENSITIVE TAPE CLOSURE POUCH

[75] Inventors: Joseph S. Sibrava, Chicago, Ill.; Frank E. Caroselli, North Arlington, N.J.

[73] Assignee: Arvey Corporation, Chicago, Ill.

[21] Appl. No.: 29,102

[22] Filed: Apr. 10, 1979

Related U.S. Application Data

[63] Continuation of Ser. No. 845,615, Oct. 26, 1977, abandoned.

[51] Int. Cl.³ ............................................. B65D 33/20
[52] U.S. Cl. ........................................ 206/439; 150/7; 229/62; 493/214
[58] Field of Search ...................... 229/62, 80; 150/7; 206/260, 439; 93/35 R

[56] References Cited

U.S. PATENT DOCUMENTS

| 3,070,280 | 12/1962 | Richmond | 229/80 |
|---|---|---|---|
| 3,203,323 | 8/1965 | Adams et al. | 229/62 |
| 3,363,828 | 1/1968 | Foglia et al. | 229/62 |
| 3,420,433 | 1/1969 | Bostwick | 229/80 |
| 3,604,616 | 9/1971 | Greif | 229/55 |
| 3,990,626 | 11/1976 | Goodrich | 229/55 |
| 3,991,881 | 11/1976 | Augurt | 206/439 |
| 4,084,689 | 4/1978 | Yamagata | 229/62 |

FOREIGN PATENT DOCUMENTS

| 875950 | 7/1971 | Canada | 229/62 |
|---|---|---|---|
| 2518229 | 11/1975 | Fed. Rep. of Germany | 206/260 |
| 491796 | 9/1938 | United Kingdom | 229/80 |

Primary Examiner—Stephen P. Garbe
Attorney, Agent, or Firm—Dressler, Goldsmith, Shore, Sutker & Milnamow, Ltd.

[57] ABSTRACT

A sterilizable pouch comprising first and second opposing webs sealed together along two peripheral side edges. An unsealed edge of the first web extending beyond the opposing lip edge of the second web to form a flap. One of the webs having sealing means disposed adjacent to and spaced from the lip edge of the second web. The sealing means having sufficient width to permit sealing of both (a) the space on the web with the sealing means defined by the border of the sealing means and the lip edge of the second web and (b) an area on the web without sealing means adjacent the lip edge sufficient to form a contaminant-proof seal when the flap is closed and sealed.

13 Claims, 5 Drawing Figures

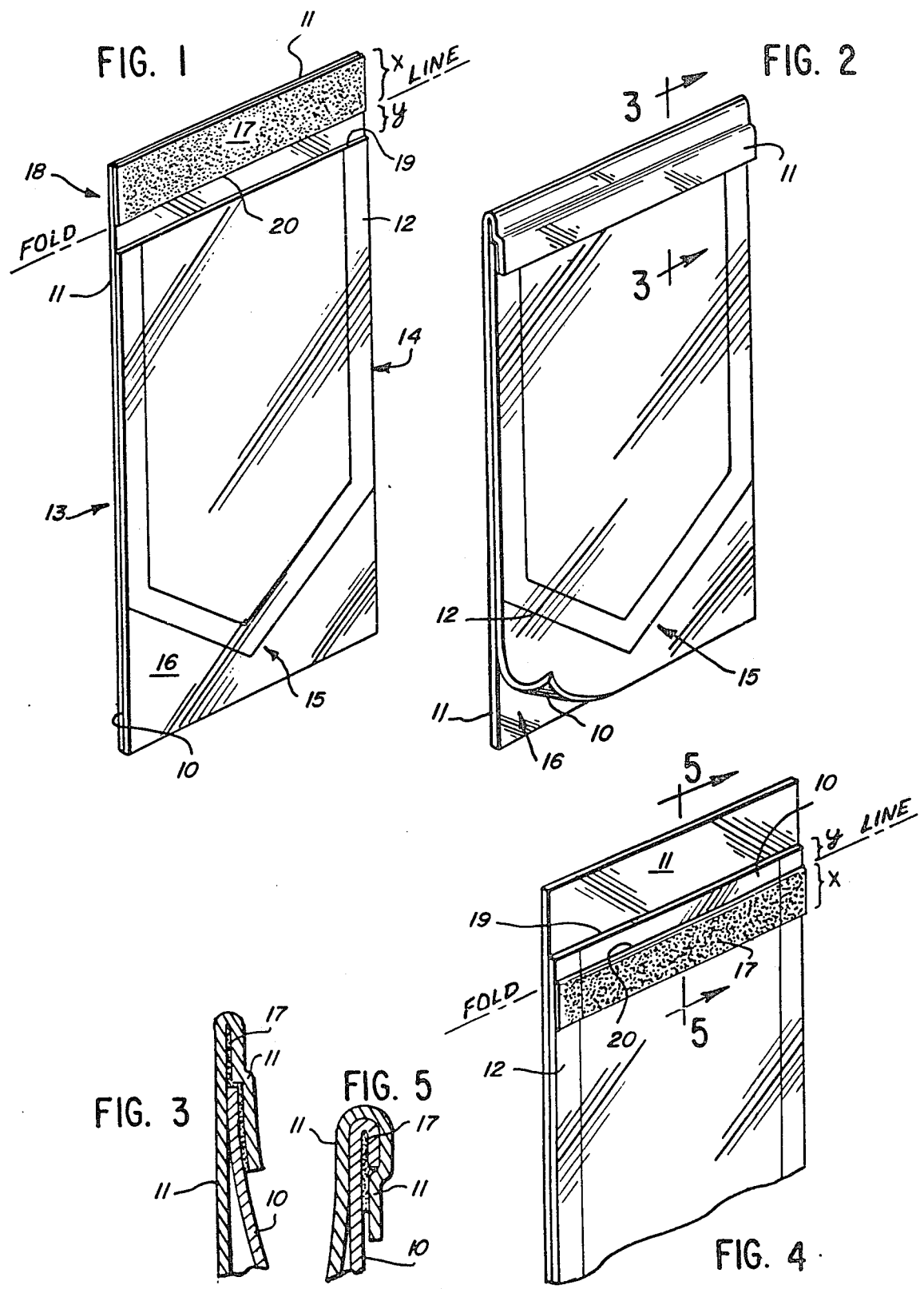

PRESSURE SENSITIVE TAPE CLOSURE POUCH

This is a continuation of application Ser. No. 845,615, filed Oct. 26, 1977, now abandoned.

BACKGROUND OF THE INVENTION

The present invention relates to disposable sterilizable pouches used in medical facilities to sterilize articles used to care for patients. More particularly the present invention is directed to a pouch that is easy to use, self sealing and maintains a contaminant proof seal after sterilization.

In recent years there has been substantial promotion of the use of disposable pouches such as shown in U.S. Pat. Nos. 3,604,616; 3,819,106; and 3,420,443. There has also been development of self-sealing envelopes such as illustrated in U.S. Pat. No. 3,070,280. However, the development did not meet all the requirements of the medical field. Surprisingly a self-sealing pouch has now been developed that is convenient to use, economical, does not require special heat sealing equipment or hand tape application, which remains contaminant proof for long time periods and which also indicates if the seal has been tampered with or broken.

SUMMARY OF THE INVENTION

A sterilizable pouch comprising first and second opposing webs sealed together along two peripheral side edges. An unsealed edge of the first web extending beyond the opposing lip edge of the second web to form a flap. One of the webs having sealing means disposed adjacent to and spaced from the lip edge of the second web. The sealing means having sufficient width to permit sealing of both (a) the space on the web with the sealing means defined by the border of the sealing means and the lip edge of the second web and (b) an area on the web without sealing means adjacent the lip edge sufficient to form a contaminant-proof seal when the flap is closed and sealed.

BRIEF DESCRIPTION OF THE EMBODIMENTS OF THE DRAWINGS

FIG. 1 is a front perspective view showing the invention in an embodiment of an unsealed pouch having pressure sensitive adhesive on the flap portion of a web;

FIG. 2 is a front perspective view of the pouch of FIG. 1 in the sealed position;

FIG. 3 is a view of the sealed pouch of FIG. 2 along lines 3—3.

FIG. 4 is a front perspective view of an unsealed pouch showing the invention in an embodiment of an unsealed pouch having pressure sensitive adhesive on a web;

FIG. 5 is a partial cutaway view of the seal of the embodiment of FIG. 4 along lines 5—5.

DETAILED DESCRIPTION OF THE INVENTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated.

Pouches according to the present invention suitably comprise two opposing webs. Web 10 is preferably a transparent thermally stable material such as coated or laminated polyethylene terephthalate (Mylar). Web 10 is sealed to opposing web 11 by heat seal 12. Web 11 is preferably made of a steam permeable paper to permit the pouch to undergo autoclave sterilization.

In a pouch of generally rectangular configuration the seal along respective pouch sides 13 and 14 is suitably a straight line along the side edges. Bottom seal portion 15 may be chevron shaped leaving the webs unsealed in pouch area 16 to provide gripping means as is illustrated in FIG. 2. The chevron shaped seal and gripping means cooperate to permit easy opening of the pouch.

Adhesive means 17 may be applied across the surface of web 11 to a portion of flap area 18 as shown in FIG. 1. The adhesive means is preferably a pressure sensitive adhesive which will be more fully discussed below. The positioning of the adhesive is of critical importance to the invention.

In the embodiment shown in FIG. 1 the adhesive is spaced a distance y from upper unsealed lip 19 of web 10. The distance y the adhesive is spaced from lip 19 and the width x of the pressure sensitive adhesive are suitably related so that the width of the adhesive is broad enough to cover an area adjacent each side of lip 19 to form a continuous seal to prevent contamination of the contents of the pouch after sterilization. It has been found preferable to use an adhesive width x of about $\frac{3}{4}$ of an inch when the distance of space y is about $\frac{3}{8}$ of an inch. Thus, when the flap is closed the adhesive covers equal areas of $\frac{3}{8}$ of an inch on either side of lip 19. It should be appreciated that distance y that the adhesive is spaced from lip 19 may vary from about $\frac{3}{8}$ of an inch to $\frac{1}{2}$ inch or more. Similarly width x of the adhesive may also vary from about $\frac{3}{4}$ of an inch to one inch or more provided that the relationship of distance y and adhesive width x is sufficient to maintain a contaminant proof seal.

The adhesive of the invention is suitably a pressure sensitive adhesive that permits the pouch to self seal upon closing and the application of pressure along the adhesive area.

Pressure sensitive transfer tape or double coated pressure sensitive transfer tape may be used in the invention. The selection of the pressure sensitive adhesive is of particular importance. The adhesive selected should be formulated from materials meeting Food and Drug Administration requirements for adhesives under FDA Section 121.2520. Suitably the adhesive selected should give bonds that maintain contaminant proof integrity from −30° F. to +350° F. Pressure sensitive adhesive tapes are normally provided with release liners which has not been shown on the drawing.

The adhesive of the invention should also be selected to provide sufficient holding strength to the paper web to tear at least a portion of the web if the closure at the pressure sensitive seal is opened. In this manner a telltale is provided to give a clear warning that the pouch has been opened and the sterile seal has been broken. This will avoid accidental resealing of a sterilized pouch.

The bond strength of the adhesive should be minimally strong enough to cause fiber tear of the paper web whereby paper fibers visibly stick to the adhesive. It is also suitable for the pressure sensitive adhesive to bond with sufficient strength to the paper that the paper web is caused to tear when the pressure sensitive closure is opened.

Illustrative performance date for the pressure sensitive adhesive is a peel strength according to PSTC-3 of 30 minutes dwell 40 oz./in, and a 24 hour dwell 50 oz./in. A shear strength of 165 hours pursuant to PSTC-7 for 1,000 gm at room temperature.

The embodiment of FIG. 2 shows the invention illustrated in FIG. 1 in a closed position.

The closure of FIG. 2 is obtained by folding flap 18 along the fold line generally defined by edge 20 the adhesive edge nearest lip 19. The flap is folded over which essentially seals paper web 11 to itself and to the area on web 10 as is illustrated in FIG. 3.

An alternative embodiment of the invention is illustrated in FIG. 4 which shows the pressure sensitive adhesive strip disposed on the surface of web 10. As previously explained, the web is spaced a distance y from lip 19 and the distance of space y and the width x of the adhesive are cooperatively selected to provide a contaminant proof seal. The closure of FIG. 4 is made by folding along a fold line generally defined by the edge of adhesive nearest lip 19. The closed pouch of FIG. 4 is shown in FIG. 5 and as may be seen the film of web 10 is sealed to itself and to the flap of web 11 to form a contaminant proof seal.

While preferred embodiment have been shown and described, it will be appreciated that other modifications may be made without departing from the spirit of the invention. For example thermally stable films other than Mylar such as nylon may be used. The thermally stable films may be coated with materials in order to permit the thermally stable film to be heat sealed to the opposing web.

It is also possible to use the present invention for gas sterilized pouches and for radiation sterilized medical pouches.

We claim:

1. A sterilizable pouch comprising first and second opposing webs, said first web including a flap extending outwardly beyond one edge of the second web, said edge of said second web being free of said first web to provide an open mouth for said pouch, one of said webs being made from a transparent thermally stable material and the other said web being made of a steam permeable paper, said first and second webs being sealed to one another around the sides and bottom thereof to close said pouch except for said open mouth, sealing means for closing the mouth of said pouch and including a strip of adhesive on one of said webs adjacent to and spaced from said open mouth, thereby defining an adhesive free zone between said adhesive strip and said open mouth, means forming a fold line at the edge of said adhesive strip closest to said open mouth, said adhesive having a width that is greater than the width of the adhesive free zone whereby when said flap is folded about said fold line (a) said open mouth is sealed by said adhesive strip, and (b) the area from said fold line to said open mouth and throughout said adhesive free zone and an area on the web without said adhesive strip adjacent to said open mouth are engaged by said adhesive strip, to thereby form a contaminant-proof seal in said mouth, said adhesive strip having sufficient holding strength to said paper web to tear at least a portion of said paper web if said seal is opened, to thereby provide a telltale that the seal has been opened and avoid accidental resealing of a sterilized pouch.

2. The sterilizable pouch of claim 1 in which said pouch is generally rectangular in shape.

3. The sterilizable pouch of claim 1 in which the seal of the bottom is a chevron-shaped seal.

4. The sterilizable pouch of claim 1 in which said adhesive is a pressure sensitive adhesive and is disposed on the surface of the flap of the first web.

5. The sterilizable pouch of claim 1 in which said adhesive strip includes a pressure sensitive adhesive and is disposed on the surface of the second web.

6. The sterilizable pouch of claim 1 in which said adhesive strip includes a pressure sensitive adhesive and said strip is spaced about ⅜ of an inch from the edge of the second web.

7. The sterilizable pouch of claim 1 in which said adhesive strip includes a pressure sensitive adhesive and has a width of about ¾ of an inch.

8. A steam-sterilizable, self sealing pouch of generally rectangular shape comprising a first web of a thermally stable transparent film, a second generally coextensive web of a steam permeable paper, having the sides and the bottom of the webs sealed together thereby leaving an unsealed end, the bottom seal being chevron shaped; the steam permeable paper web extending beyond the unsealed end of the film web to define a flap, pressure sensitive adhesive sealing means positioned across the flap to its side edges, said pressure sensitive adhesive having a width of about ¾ of an inch and spaced about ⅜ of an inch from the unsealed end of the film web thereby defining an adhesive free zone, the edge of the pressure sensitive adhesive nearest the film web generally defining a fold line whereby when the pouch is sealed closed the flap is sealed to itself from said fold line to said open mouth and throughout said adhesive free zone and to the first film web to form a contaminant proof seal, said adhesive means having sufficient holding strength to the paper after sterilization to tear at least a portion of the paper structure when the pressure sensitive end closure is opened to thereby provide a telltale that the seal has been opened and avoid accidental resealing of a sterilized pouch.

9. A steam-sterilizable, self sealing pouch of generally rectangular shape comprising a first web of a thermally stable transparent film, a second web of a steam premeable paper, having the sides and the bottom of the webs sealed together thereby leaving an unsealed end, the bottom seal being chevron shaped; the paper web extending beyond the film web to define a flap, pressure sensitive adhesive sealing means equal in length to the size of the unsealed end positioned across the film web and spaced about ⅜ of an inch from the unsealed end of the film web thereby defining an adhesive free zone, the width of the pressure sensitive adhesive sealing means being about ¾ of an inch, the edge of the adhesive nearest the unsealed end generally defining a fold line whereby when the pouch is sealed closed the film is sealed to itself from said fold line to said open mouth and throughout said adhesive free zone and to the flap to form a contaminant proof seal, said adhesive means having sufficient holding strength to the paper after sterilization to tear at least a portion of the paper structure when the pressure sensitive end closure is opened to thereby provide a telltale that the seal has been opened and avoid accidental resealing of a sterilized pouch.

10. A method of manufacturing a sterilizable pouch comprising aligning first and second webs in opposing edge to edge position, said first web including a flap extending outwardly beyond one edge of the second web, sealing said opposing webs along three opposing side edges to form a pouch having an open mouth at the edge of the second web opposite said flap, applying an adhesive means to one of said webs adjacent to and spaced from said open mouth, forming a fold line at the edge of said adhesive strip closest to said open mouth, said adhesive having a sufficient width whereby when said flap is folded about said fold line (a) said open mouth is sealed by said adhesive means, and (b) the area from said fold line to said open mouth and throughout said adhesive free zone and an area on the web without said adhesive means adjacent to said open mouth are engaged by said adhesive means to thereby form a contaminant-proof seal in said pouch.

11. A sterilizable pouch comprising first and second opposing webs, one of said webs being made from a plastic material and the other said web being made of a steam permeable paper, means defining an open mouth for said pouch, said first and second webs being sealed to one another to close said pouch except for said open mouth, sealing means for closing the mouth of said pouch and including a strip of adhesive on one of said webs adjacent to and spaced from said open mouth, thereby defining an adhesive free zone between said adhesive strip and said open mouth, means forming a fold line at the edge of said adhesive strip closest to said open mouth, said adhesive strip having a width that is greater than the width of the adhesive free zone whereby when said pouch is folded about said fold line (a) said open mouth is sealed by said adhesive strip, and (b) the area from said fold line to said open mouth and throughout said adhesive free zone and an area on the web without said adhesive strip adjacent to said open mouth are engaged by said adhesive strip, to thereby form a contaminant-proof seal in said mouth.

12. A sterilizable pouch having a width dimension and a length dimension, said pouch comprising: first and second opposing webs, one of said webs being made from a plastic material and the other said web being made of a steam permeable paper, means defining an open mouth for said pouch, said open mouth extending widthwise of said pouch perpendicular to the pouch length dimension and adjacent to and parallel with one pouch end, the width dimension of said open mouth being less than the width dimension of said pouch, said first and second webs being heat-sealed to one another to close said pouch except for said open mouth, sealing means for closing the mouth of said pouch and including a widthwise extending generally rectangular strip of pressure sensitive adhesive on said other web adjacent to and in spaced parallel relationship with said open mouth, thereby defining a rectangularly shaped adhesive free zone between said adhesive strip and said open mouth, said adhesive strip extending completely across the width dimension of said pouch so as to be wider than said open mouth, means forming a fold line at the edge of said adhesive strip closest to said open mouth, said adhesive strip having a lengthwise dimension that is greater than the lengthwise dimension of the adhesive free zone whereby when said pouch is folded about said fold line (a) said open mouth is sealed by said adhesive strip, and (b) the area from said fold line to said open mouth and throughout said adhesive free zone, an area on the web without said adhesive strip adjacent to said open mouth and areas outwardly of each end of the open mouth are all engaged by said adhesive strip, to thereby form a contaminant-proof seal in said mouth.

13. The sterilizable pouch of claim 12 in which said other web extends outwardly from one end of said one web to define a flap, and wherein said adhesive strip extends across the free end of said flap.

* * * * *